United States Patent [19]

Tuy et al.

[11] Patent Number: 5,592,523

[45] Date of Patent: Jan. 7, 1997

[54] TWO DIMENSIONAL DETECTOR ARRAY FOR CT SCANNERS

[75] Inventors: Heang K. Tuy, Chesterland; Dale J. Bendula, Painesville; Walter W. Lindstrom, Shaker Heights, all of Ohio

[73] Assignee: Picker International, Inc., Highland Heights, Ohio

[21] Appl. No.: 350,412

[22] Filed: Dec. 6, 1994

(Under 37 CFR 1.47)

[51] Int. Cl.$^6$ .................................................. H05G 1/60
[52] U.S. Cl. ............................................ 378/19; 378/98.8
[58] Field of Search ............... 378/98.8, 19; 250/370.09, 250/370.11

[56] References Cited

U.S. PATENT DOCUMENTS

| | | | |
|---|---|---|---|
| Re. 32,164 | 5/1986 | Kruger | 378/19 |
| Re. 32,779 | 11/1988 | Kruger | 378/19 |
| 3,507,734 | 4/1970 | Ruderman | 156/268 |
| 3,529,161 | 9/1970 | Oosthoek et al. | 250/83.3 |
| 3,717,762 | 2/1973 | Grenier et al. | 250/71.5 R |
| 3,936,645 | 2/1976 | Iversen | 250/486 |
| 4,055,765 | 10/1977 | Gerber et al. | 250/370 |
| 4,609,823 | 9/1986 | Berger et al. | 250/370.09 |
| 4,652,760 | 3/1987 | Kondo et al. | 250/363 |
| 4,672,542 | 6/1987 | Roux et al. | 364/414 |
| 4,688,175 | 8/1987 | Kaneko et al. | 364/414 |
| 4,831,262 | 5/1989 | Govaert et al. | 250/363.01 |

(List continued on next page.)

OTHER PUBLICATIONS

"Reduced Dose and Improved Image Quality with a Computerized Line–Scan Radiography System", Sashin, et al., IEEE Trans. on Med. Imaging, vol. 12, No. 2, (1993) pp. 380–383.

Tuy, Heang K., "An Inversion Formula for Cone–Beam Reconstruction", Siam J. Appl. Math., vol. 43, No. 3, Jun. 1983, pp. 546–552.

Feldkamp, L. A., "Practical Cone–Beam Algorithm", J. Opt. Soc. Am. A./vol. 1, No. 6, Jun. 1984, pp. 612–619.

Grangeat, Pierre, "Mathematical Framework of Cone Beam 3D Reconstruction Via the First Derivative of the Radon Transform", LETI, Nov. 1990, pp. 1–32.

Fossum, Eric R., "Architectures for Focal Plan Image Processing", Optical Engineering, vol. 28, No. 8, Aug. 1989, pp. 865–871.

Fossum, Eric R., "Charge–Domain Analog Signal Processing for Detector Arrays" Nuclear Instruments and Methods in Physics Research, Mar. 1989, pp. 530–535.

*Primary Examiner*—Don Wong
*Attorney, Agent, or Firm*—Fay, Sharpe, Beall, Fagan, Minnich & McKee

[57] ABSTRACT

A CT scanner (10) includes a reconstruction processor (82) for reconstructing an image from digital signals from detector arrays (20). Each detector array includes scintillation crystals (22) arranged in an array for converting x-ray radiation into visible light. An array of photodetectors (24) is mounted beneath the scintillation crystal array for converting light emitted from the scintillation crystals into electrical charge. The combination scintillation crystal, photodetector array is mounted to and preferably integral with an integrated circuit (26) having charge storage devices (32, 34). Electrical charge generated by each photodetector is integrated and stored alternately by a corresponding pair of charge storage devices. The charge storage devices operate as a double buffer in which one charge storage device accumulates charge while the other holds an accumulated charge until read out by downstream circuitry. The downstream circuitry includes a plurality of amplifiers (66) and an analog digital converter (62) integrally formed on the substrate. The analog to digital converter converts analog signals corresponding to the stored charges into digital values. The digital valves created on the detector arrays are transferred in digital form to the reconstruction processor.

19 Claims, 5 Drawing Sheets

U.S. PATENT DOCUMENTS

| | | | |
|---|---|---|---|
| 4,879,464 | 11/1989 | Iinuma | 250/361 R |
| 4,891,829 | 1/1990 | Deckman et al. | 378/4 |
| 4,937,453 | 6/1990 | Nelson | 250/370.09 |
| 4,965,726 | 10/1990 | Heuscher et al. | 364/413.19 |
| 4,980,553 | 12/1990 | Henry | 250/369 |
| 5,093,575 | 3/1992 | Perusek | 250/363.08 |
| 5,099,128 | 3/1992 | Stettner | 250/370.11 |
| 5,117,114 | 5/1992 | Street et al. | 250/370.11 |
| 5,150,394 | 9/1992 | Karellas | 378/62 |
| 5,170,439 | 12/1992 | Zeng et al. | 382/6 |
| 5,187,369 | 2/1993 | Kingsley et al. | 250/370.11 |
| 5,377,250 | 12/1994 | Hu | 378/15 |

TWO DIMENSIONAL DETECTOR ARRAY FOR CT SCANNERS

BACKGROUND OF THE INVENTION

The present application relates to the art of medical diagnostic imaging in which penetrating radiation is received by radiation sensitive detectors. The application subject matter finds particular use in computerized tomographic (CT) scanners and will be described with particular reference thereto. However, the invention may also find use in connection with other diagnostic imaging modalities, industrial quality assurance imaging, video camera imaging, and the like.

Heretofore, CT scanners have included a plurality of discrete radiation detectors which converted X-ray radiation which traversed a patient examination area into electronic signals. Each radiation detector included a radiation sensitive face, such as a scintillation crystal, which converted the received radiation into a corresponding quantity of light. A solid state photodiode was provided to convert the light emitted by the scintillation crystal into analog electrical signals indicative of the intensity of the crystal emitted light, hence the intensity of the received radiation.

The radiation detectors were separately arranged on a circuit board. Each circuit board supported a linear array of photodiodes and attached scintillation crystals. In addition, a preamplifier was attached to the circuit board and connected to each photodetector output to convert the photodiode current to an appropriate voltage within the dynamic range of the analog-to-digital conversion system.

The analog signals from the circuit board were carried to a central processing area where they were converted from their analog state into a corresponding digital signal. The analog signals were carried to the central processing area via a long bus system which extended around the scanner.

One problem relates to degradation of the analog signals as they travel over the long bus system between the radiation detectors and the central processing area.

CT scanners operate in a sea of extraneous radio frequency electromagnetic signals, the frequencies of which vary over a wide band. Sources of extraneous signals include nearby operating electrical components, equipment, signals from other detectors, and the like. The long bus systems include long lead wires which inadvertently act as antennas in picking up extraneous electromagnetic signals and converting them into analog signals. The extraneous analog signals are superimposed on and mix with the analog signals from the detectors. The superimposed extraneous signals appear as noise and fictitious data when reconstructed into images. The resulting images are degraded by noise, ghosting, and other artifacts.

Prior art scanners commonly collected data from a single slice or a small plurality of slices. To scan a volume, the patient was shifted longitudinally either incrementally after each slice to generate a multiplicity of parallel slices or continuously for a helical scan. The multiple rotation of the x-ray beam around the subject was time-consuming and stressful on the x-ray tube and generator.

SUMMARY OF THE INVENTION

In accordance with the present invention, a CT scanner is provided in which a plurality of two dimensional detector arrays output parallel streams of digital signals to a remotely located central processing area. The plurality of detector arrays are positioned opposite a radiation source and receive x-ray radiation having traversed a patient examination area. Each area detector array includes an array of scintillation crystals which convert x-ray radiation into visible light. A plurality of photodetectors are arranged in an array and aligned with the scintillation crystals so that light emitted from each scintillation crystal is converted into electrical charge by the aligned photodetector. First and second charge storage devices are integrally formed on a substrate for accumulating and storing charges generated by the photodetectors. The first and second charge storage devices accumulate charge generated by the photodetectors in a dual mode wherein one detector accumulates charge while charge accumulated on the other is read-out by downstream circuitry. The downstream circuitry is also integrally formed on the substrate and includes a plurality of amplifiers for boosting analog signals representative of the accumulated charges, and a multiplexer which multiplexes analog signals outputted by the amplifiers onto a single line. An analog to digital converter is connected to the output of the multiplexer and converts the analog signals into digital counterparts prior to being conveyed to the central processing area.

One advantage of the present application is that signals outputted by the radiation detector arrays are in digital form and are immune from the effects of surrounding extraneous radiation.

Another advantage of the present invention is that it facilitates acquiring a good quality signal at a very high rate.

Another advantage of the present invention is provided by the dual mode method of integrating photodetector charge which increases the speed at which digital signals can be outputted by the detector arrays.

Another advantage of the present invention is that the scintillation crystal array, the photodetector array, the amplifier, and the analog-to-digital converter can be formed integrally with the substrate to provide a fully integrated hybrid circuit using conventional manufacturing techniques.

Still further advantages will become apparent to those of ordinary skill in the art upon reading and understanding the following detailed description.

BRIEF DESCRIPTION OF THE DRAWINGS

The invention may take form in various components and arrangements of components. The figures are only for purposes of illustrating preferred and alternate embodiments and are not to be construed as limiting the invention.

DETAILED DESCRIPTION OF THE PREFERRED EMBODIMENT

Figure 1:
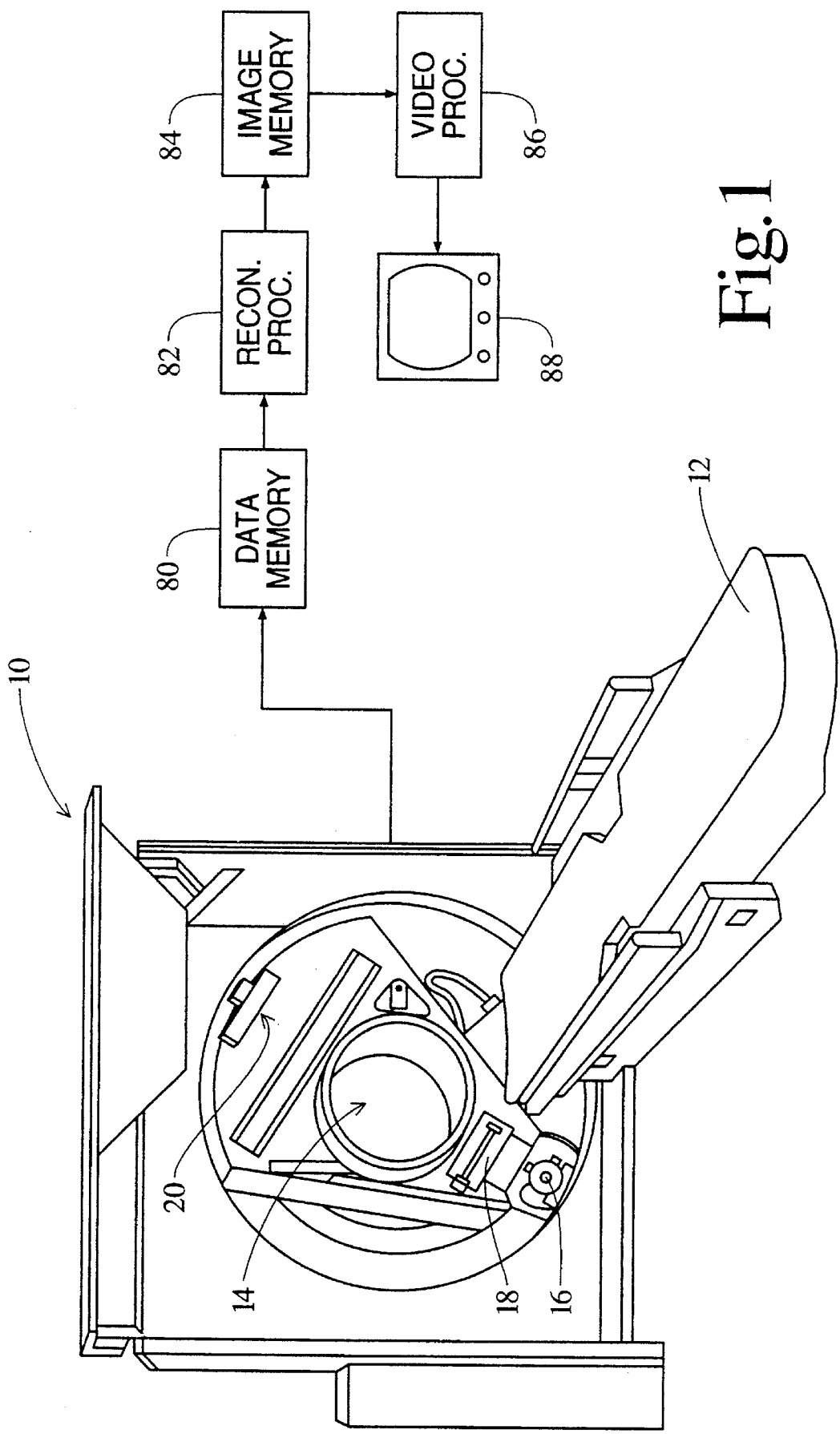
FIG. 1 illustrates a CT scanner employing a two-dimensional detector array in accordance with of the present invention.

With reference to FIG. 1, a CT scanner 10 selectively images regions of a patient supported by a patient table 12 in a scan circle or examination region 14. The patient table is positionable longitudinally. The CT scanner has an x-ray tube 16 which emits a beam of x-rays toward an area of the patient being examined. In the preferred embodiment, a collimator 18 collimates the x-rays into a cone beam. When the examination area is irradiated with the x-ray energy, a percentage of the x-rays reaching the examination area is absorbed by the patient's body. The amount of absorption depends on the density of bone or tissue upon which the x-rays are incident. The x-ray energy of the x-rays exiting the patient's body along each ray represents a linear integration of the radiation absorption of each incremental patient element along the ray. The absorption is indicative of relative tissue and skeletal densities.

Figure 2:
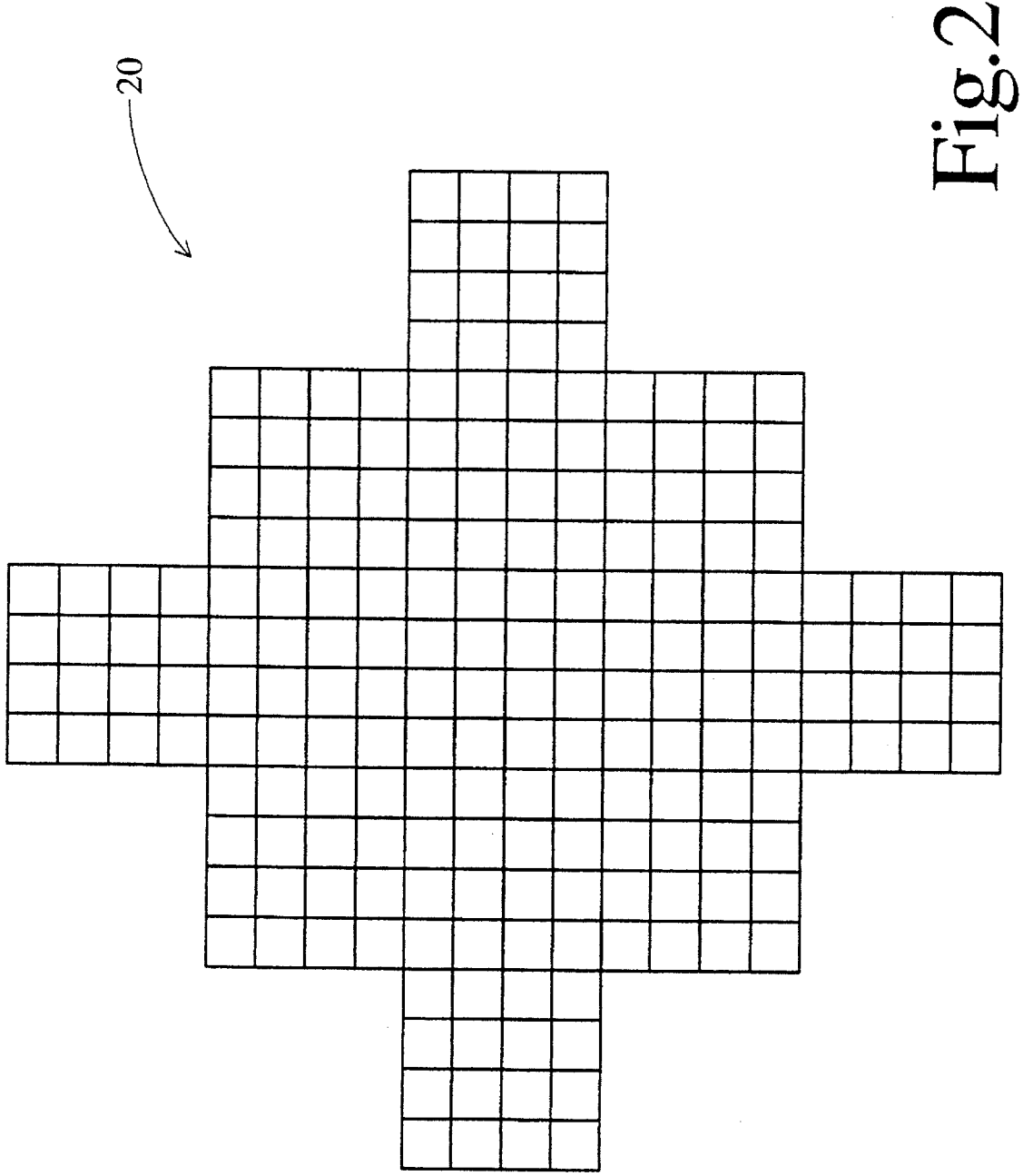
FIG. 2 illustrates an array of detector arrays of the CT scanner of FIG. 1 arranged for use in receiving cone-shaped x-ray beams.

With continued reference to FIG. 1 and with further reference to FIG. 2, a plurality of detector arrays 20 receive radiation which has traversed the examination area. In the illustrated embodiment, thirteen arrays are arranged to receive a circular or rectangular cross-sectioned cone of radiation. Each array is disposed along a plane normal to the center line of the cone shaped x-ray beam and is mounted for rotation with the x-ray beam. Cone shaped beams allow a larger volumetric region of the patient to be imaged per unit of time when compared with a patient region imaged using conventional fan shaped beams.

Figure 3:
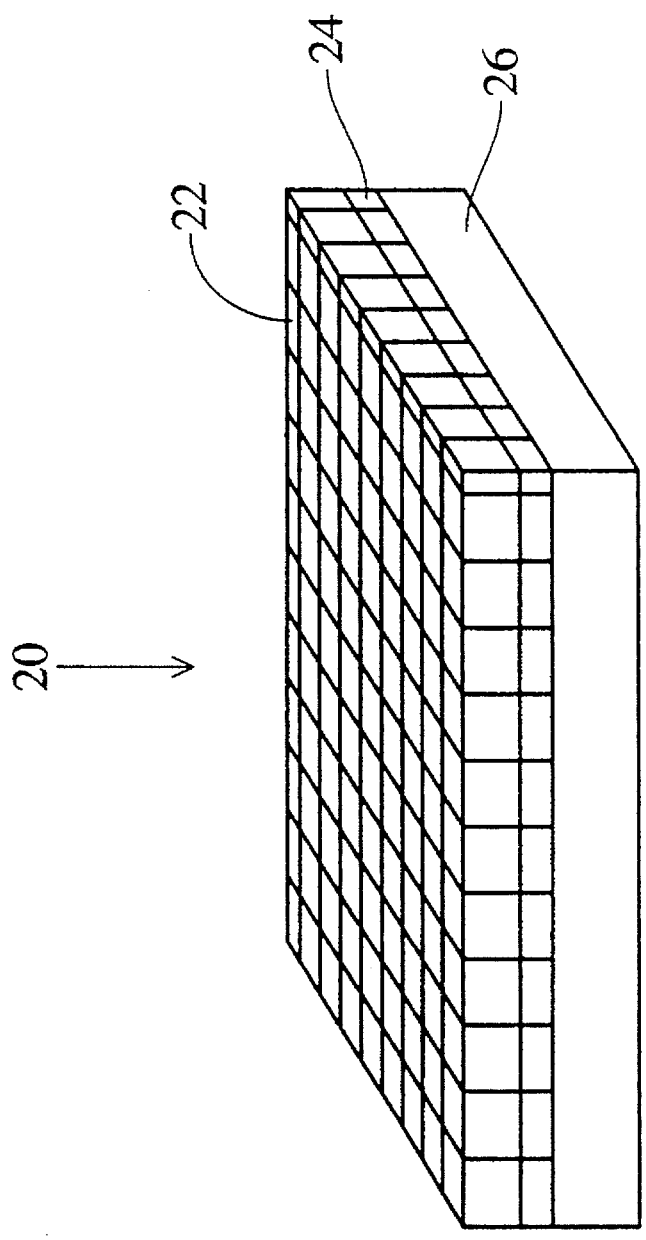
FIG. 3 illustrates a scintillation crystal and photodetector array in combination with an integrated circuit.

With continued reference to FIG. 2 and with further reference to FIG. 3, each detector array 20 includes an n×m array of scintillation crystals 22 and photodetectors 24 connected or preferably integrated into an integrated circuit 26. The scintillation crystal photodetector array is covered with a light opaque, x-ray transmissive covering (not shown) to prevent extraneous light from reaching the crystals or photodetectors. The scintillation crystal and photodetector arrays are preferably fully integrated with the integrated circuit using conventional solid-state component manufacturing techniques. However, description will further be made with respect to scintillation crystals and photodetectors which are connected to the integrated circuit using conventional bonding techniques.

The scintillation crystals 22 are formed from cadmium tungstate or other similar materials capable of generating visible light upon being excited with x-ray radiation. The preferred embodiment uses a 16×16 array of scintillation crystals of 1 mm square area. It should be understood that a greater or lesser number of scintillation crystals of varying widths can also be employed without departing from the inventive concept of the present application. Each scintillation crystal of the 16×16 array is optically coupled to one of the photodetectors 16×16 array of photodetectors using conventional optical coupling cement, or the like.

During a typical x-ray examination, the patient is placed between the x-ray source and the detector arrays. The scintillation crystals convert x-rays that are transmitted through the examination area of the patient to corresponding photons of light. The photodiodes convert the light photons to electrical signals indicative of the integrated x-ray absorption along the corresponding ray.

X-rays that have traversed the examination area are received through the front face of the scintillation crystal. The scintillation crystal converts these x-rays into visible light of a characteristic wavelength. The visible light exits each scintillation crystal via a surface that is optically coupled to one of the photodetectors. The scintillation crystals are covered on all surfaces except the surface which is optically coupled to the photodetector with an x-ray transmissive, optical light opaque coating (not shown), e.g., an aluminum coating. Preferably, the coating is reflective such that substantially all light is reflected to the photodetector. Spatial intensity patterns of light emitted from the scintillation crystal array are proportional to spatial patterns of the x-ray radiation having traversed the examination area.

One of the scintillation crystals is mounted on a photodetector of the 16×16 array of photodetectors to convert the light emitted from the scintillation crystal into discrete electrical charge. The preferred embodiment uses a 16×16 array of photodetectors of one square millimeter area each. It should be understood that other numbers of photodetectors and scintillation crystals can be used. The technology of forming a 16×16 array of photodetectors is readily available. For example, photodetectors in the form of photodiodes are generally manufactured in a continuous sheet which forms one very large photodiode. By etching or cutting the surface layer, but not the substrate, the large photodiode sheet is subdivided into an array of small photodiodes.

It should be noted that the photodetectors can be defined by devices other than photodiodes. Photocapacitors, photoresistors, charge coupled devices (CCD), and the like, are also contemplated.

Light from the scintillation crystal is converted by the photodetector into a corresponding charge value. In a photodiode, photons of light create charge pairs in an active surface layer. The charge is channeled from the active layer through detection circuitry to the substrate to create an output current that is proportional to the number of light photons received. In a charge coupled device, each cell is charged to a preselected level. Each photon of received light discharges a corresponding unit charge. The difference between the initial charge and the remaining charge is proportional to the number of photons of light received.

Figure 4:
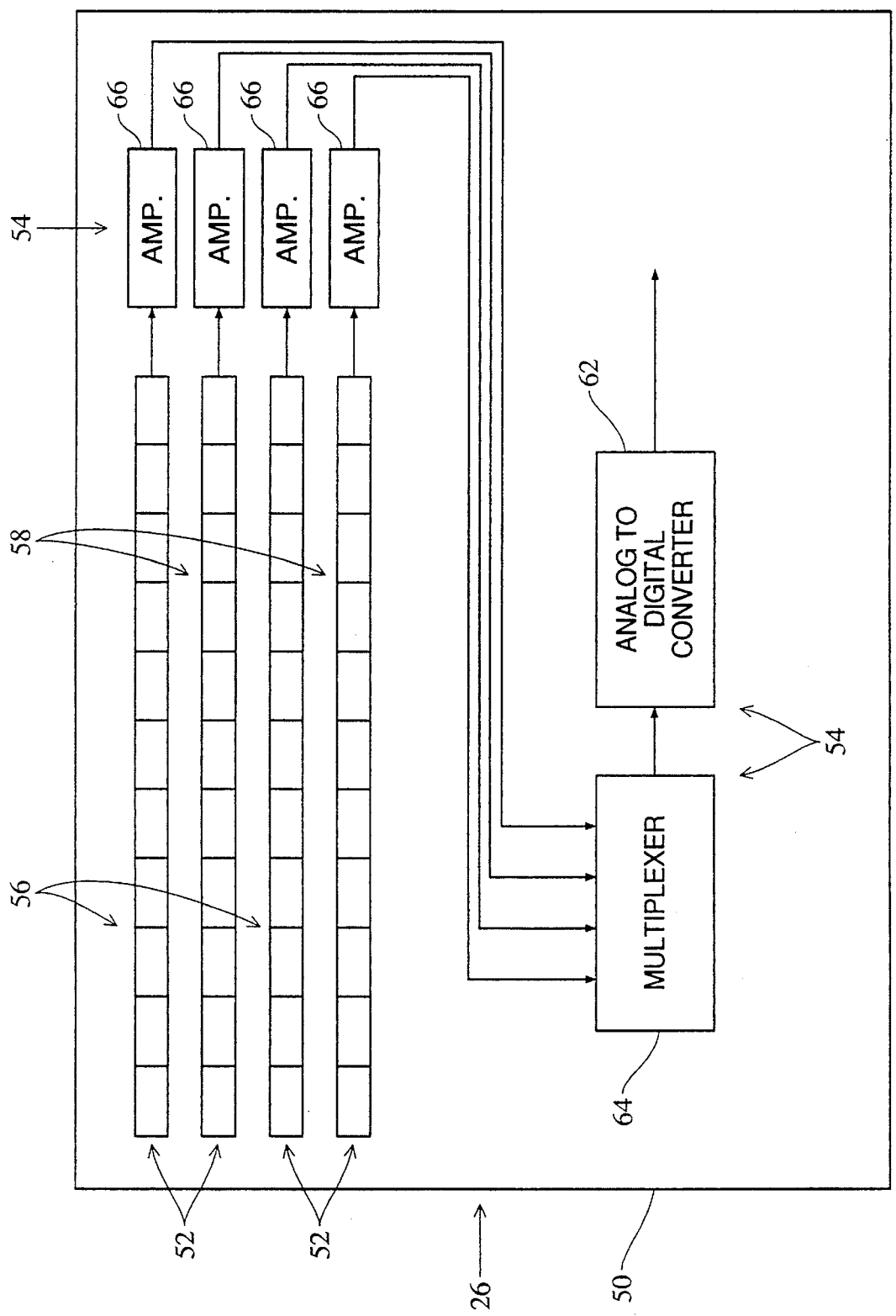
FIG. 4 is a block diagram illustrating one embodiment of the integrated circuit of FIG. 3; and, FIG. 5 is a block diagram illustrating a second embodiment of the integrated circuit.

With reference to FIG. 4, aligned beneath the photodetector array and bonded thereto is the integrated circuit 26 which processes both analog and digital signals. The integrated circuit is formed on a substrate 50 and includes charge storage devices 52, several cells of which are shown, and signal processing circuitry 54. In the FIG. 4 embodiment, the charge storage devices accumulate and store charge from the photodetectors output currents until read out by the downstream processing circuitry.

Each photodetector is connected with charge storage device cells of two distinct groups of charge storage devices 56, 58. The charge storage devices "accumulate" photodetector charge in that they store charge during an x-ray exposure interval. The first and second groups of charge storage devices operate in a dual buffer mode in which one group, while connected, accumulates charge from respective photodetectors as the other group is accessed by downstream circuitry of the integrated circuit which will be more fully explained below. It is to be appreciated that the dual buffer mode provides a faster data output from the radiation detector array.

The first and second charge storage device groups preferably take form in first and second groupings of capacitors integrally formed on the substrate. To facilitate accumulated charge output, rows of capacitors in one grouping are sequentially gated to a common bus (not shown) whereby stored accumulated charges in each row are serially accessed by downstream circuitry while capacitors in the other grouping continue to accumulate charge.

In an alternative embodiment, the first and second charge storage devices take form in charge injected devices (CID) or charge coupled devices (CCD). The CCDs or CIDs are interconnected in rows to form an analog shift register. Accumulated charges in each row are serially shifted until read by downstream circuitry. Again, one of the first or second groups accumulates photodetector generated charges while the other group is shifting accumulated charge to downstream circuitry.

The foregoing radiation detector arrays have been described as containing an array of photodetectors, each one of which is alternately connected to respective first and second charge storage devices. However, each photodetector could selectively be connected to a single charge storage device without departing from the inventive concept of the present application. To maintain the dual buffer mode described above, the photodetectors in this embodiment function as charge storage devices in addition to functioning as a device for converting light into electrical charge. For example, photodetectors in the form of photocapacitors accumulate charge generated thereby during an x-ray examination interval. At the end of the x-ray examination interval, the accumulated charges in each photocapacitor are transferred to a respective charge storage device. Thereafter, charges stored on the charge storage device are sequentially read out by downstream circuitry while the photocapacitors accumulate further light converted electrical charge.

The integrated circuit further includes one or more analog to digital converters 62 integrally formed on the substrate and interconnected within the downstream circuitry wherein analog signals corresponding to accumulated charges are converted into digital signals. Digital signals outputted by the detector array of the present application are transferred from the rotating gantry to the stationary gantry by one or more slip rings. Optionally, a data compression circuit is used to reduce the volume of digital data transferred between the rotating gantry and stationary gantries.

The integrated circuit further includes one or more multiplexers 64 and one or more amplifiers 66 which are integrally formed on the substrate 50. The amplifiers may be selectively interconnected to the charge storage devices and boost the analog signals produced by the accumulated charges thereon.

The amplifiers are selectively interconnected to the charge storage devices such that accumulated charges from distinct charge storage devices can be boosted by the same amplifiers. For example, charge storage devices are arranged on the substrate in arrays of rows and columns. Each row of charge storage device array is selectively connected to a respective amplifier. In particular, each common bus to which a row of charge storage capacitors are sequentially gated are connected to an input of a respective amplifier. In this arrangement, accumulated charges in the row are serially inputted to the connected amplifier. Similarly, each analog shift register formed by interconnecting a row of charge coupled devices or charge injected devices, can be connected to the input of a respective amplifier. In this arrangement, charges accumulated may be shifted between adjacent charge storage devices until being inputted to an amplifier. In either arrangement, it is to be appreciated that the amplifiers output analog signals in parallel.

Figure 5:
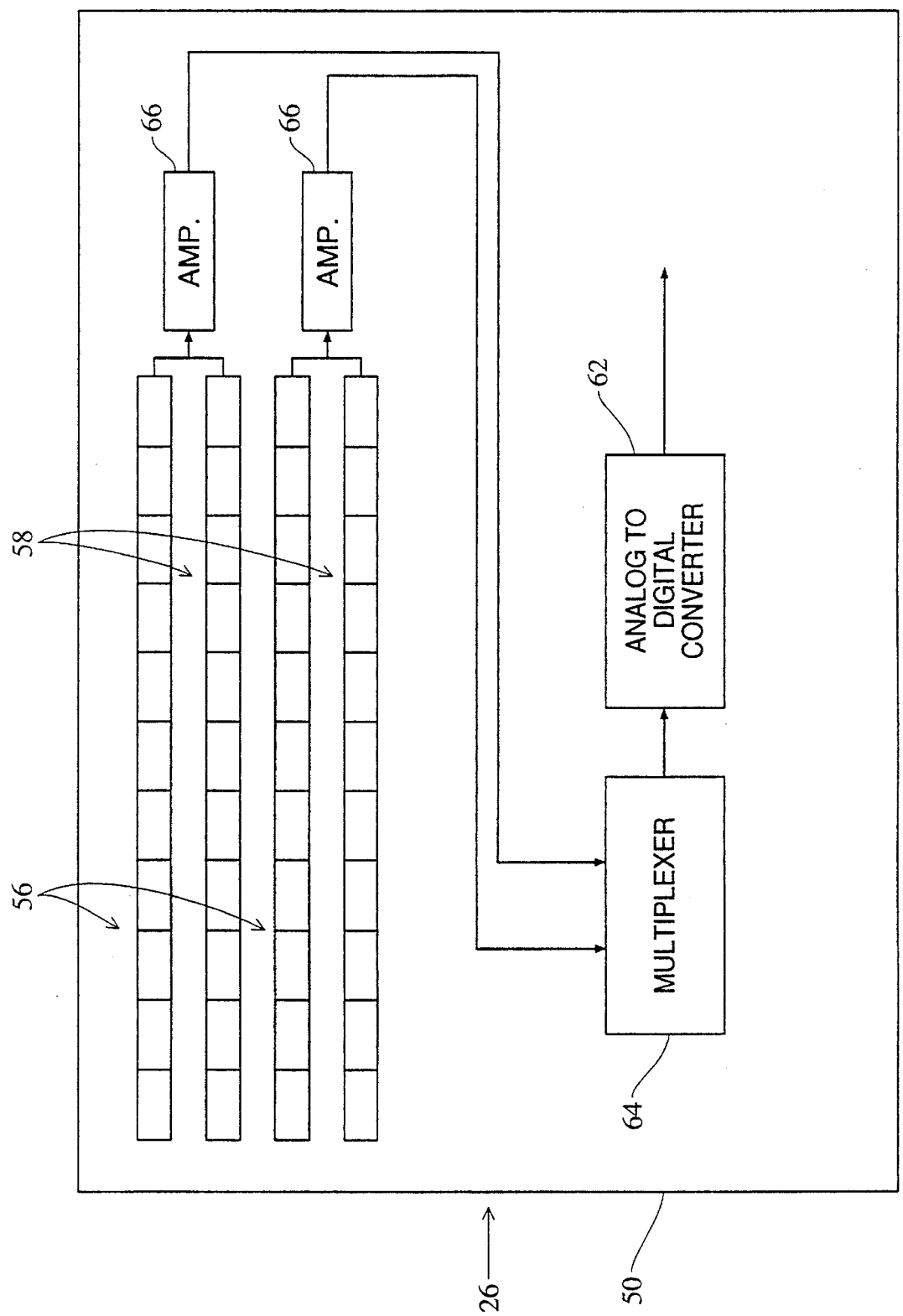

With reference to FIG. 5, in an alternative embodiment, each amplifier is alternately connected to two rows of charge storage devices which are connected with a common row of photodetectors in the double buffer configuration. In this arrangement, accumulated charges from one row of first or second charge storage devices are serially inputted to a respective amplifier while the other row is disconnected and accumulating charge generated by the photodetectors. As can be appreciated, this arrangement further reduces the number of amplifiers on the integrated circuit resulting in on board power consumption savings since amplifiers typically require relatively large currents to operate effectively.

Optionally, multiplexers are interposed between the amplifiers and the analog to digital converter. Each multiplexer is integrally formed on the substrate. In this arrangement, analog signals outputted by the amplifiers are multiplexed onto a single line prior to being converted into digital signals.

As set forth above, the analog to digital converter converts analog signals to a corresponding digital output. These digital outputs are transferred via the slip ring to the stationary gantry.

Bonding photodetectors to an integrated circuit often results in photodetectors of unequal characteristics. The photodetectors might be unequal in that they produce bias offsets which are included in charge accumulated within the detector itself or a connected charge storage device. The offset bias can be slight or extreme. However, the offset bias typically varies from detector to detector. In the extreme, offset bias causes analog signals to be biased outside the dynamic range of the amplifiers. In this situation, AC components of the analog signal which correspond to the x-ray radiation incident upon the scintillation crystals, could be filtered out inadvertently by the amplifier.

The substrate 50 further includes gates (not shown) for connecting charge storage devices to the amplifiers. In the CCD embodiment, the circuitry for sequentially clocking the charge values across the array to the amplifiers is mounted on the substrate.

The digital data from the detectors is accumulated in a data memory 80. A cone beam reconstruction processor 82 reconstructs the data into a volumetric image representation which is stored in an image memory 84. A suitable cone beam reconstruction technique is show in "An Inversion Formula for Cone-Beam Reconstruction." *SIAM Journal of Applied Mathematics*, Tuy, H. K., pp. 546–552 (1983). A video processor 86 selectively accesses data from the image memory to produced slice images, 3-D renderings, and other user requested displays for display on a video monitor ee as are customary in the art.

The present invention is also applicable to fourth generation scanners. By mounting a ring of the above-described 16×16 arrays around the stationary gantry, data for sixteen slices is collected concurrently. Of course, arrays of other sizes, such as a 4×6 array, may also be advantageous.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a computerized tomographic scanner having an x-ray radiation source for selectively emitting penetrating x-ray radiation which traverses an examination area, an image reconstruction means for reconstructing images representative of the examination area using digital signals, a plurality of radiation detector arrays positioned opposite the radiation source each detector array having (i) a plurality of scintillation crystals arranged in an n×m array, each of said scintillation crystals converting x-ray radiation into visible light, (ii) a substrate, and (iii) a plurality of photodetectors connected to the substrate, arranged in an n×m array, and optically coupled with the scintillation crystal array, each photodetector converting visible light into electrical charge, THE IMPROVEMENT COMPRISING:

a plurality of charge storage devices formed on the substrate for accumulating and storing charge, each photodetector being selectively connected to a respective charge storage device for altering the analog charge stored thereby in accordance with the charge generated in response to received light;

a plurality of amplifiers formed on the substrate and connected with the charge storage devices for selectively amplifying the stored analog charges; and an analog to digital converter formed on the substrate and connected with the amplifiers for converting the amplified analog charges into digital values.

2. A computerized tomographic scanner comprising:

an x-ray radiation source for selectively generating a beam of x-ray radiation which rotates around an examination region to traverse the examination region from a multiplicity of directions;

a plurality of area radiation detector arrays positioned across the examination region from the radiation source to receive x-ray radiation that has traversed the examination region in the multiplicity of directions, each radiation detector array including:

a substrate, a plurality of photodetectors connected to the substrate and arranged in an n×m array, a plurality of scintillation crystals arranged in an n×m array, each of said scintillation crystals converting x-ray radiation into visible light, the scintillation crystals being optically coupled to the photodetectors, a first plurality of charge storage devices formed on the substrate for accumulating and storing charge, each photodetector being connected to a respective charge storage device for altering the stored charge in accordance with the electrical charge from the respective photodetector, a plurality of amplifiers formed on the substrate for sequentially amplifying stored charges from a series of the charge storage devices to create analog signals, a plurality of analog to digital converters formed on the substrate for converting the amplified analog signals into digital signals; and an image reconstruction processor for reconstructing the digital signals into images representative of radiation transmissive properties of a subject in the examination region.

3. The computerized tomographic scanner as set forth in claim 2 wherein each radiation detector array further includes a second plurality of charge storage devices formed on the substrate for accumulating and storing charge, each photodetector being alternately connected to a respective one of the first and second charge storage devices such that while the amplifiers create the analog signal from one of the first and second charge storage devices the photodetectors alter the charge on the other of the first and second charge storage devices.

4. The computerized tomographic scanner as set forth in claim 2 wherein each radiation detector array further comprises:

a multiplexer formed on the substrate and selectively connected to the amplifiers for multiplexing the analog signals therefrom, the multiplexer being connected to the analog to digital converter for supplying the multiplexed analog signals thereto.

5. The computerized tomographic scanner as set forth in claim 2 wherein each radiation detector array further comprises:

a second plurality of charge storage devices formed on the substrate for accumulating and storing charge, each photodetector being alternately connected to a respective second charge storage device and the respective first charge storage device;

a second plurality of amplifiers connected with the second plurality of charge storage devices;

a multiplexer formed on the substrate and selectively connected to the amplifiers for multiplexing amplified analog signals; and at least a second analog to digital converter formed on the substrate and connected to an output of the multiplexer for converting the multiplexed amplified analog signals into the digital signals, the first and second analog to digital signal converters operating in parallel.

6. The computerized tomographic scanner as set forth in claim 2 wherein the charge storage devices are integrally formed in columns and rows on the substrate, charge storage devices of each row are selectively interconnected to allow accumulated charge to be shifted from adjacent charge storage device to adjacent charge storage device to serialize stored charges supplied to the amplifiers.

7. The computerized tomographic scanner as set forth in claim 2 wherein the plurality of detector arrays are themselves arranged in an array.

8. The computerized tomographic scanner as set forth in claim 7 wherein the penetrating x-ray radiation forms a cone-shaped beam and the array of radiation detector arrays conforms to a transverse cross-section of the cone beam.

9. The computerized tomographic scanner as set forth in claim 2 further including a bias offset correction for correcting a bias offset voltage produced by each of the photodetectors.

10. The computerized tomographic scanner as set forth in claim 2 wherein the photodetectors, charge storage devices, and amplifiers are integrally formed on the substrate.

11. The computerized tomographic scanner as set forth in claim 10 wherein the scintillation crystals are integrally formed on the substrate.

12. A radiographic scanner comprising:

a source of penetrating radiation for selectively irradiating an examination region with a beam of penetrating radiation;

at least one radiation detector array disposed across the examination region from the source for receiving penetrating radiation that has traversed the examination region, the detector array including:

a substrate, an array of charge storage devices formed on the substrate for storing electrical charge, a plurality of amplifiers disposed on the substrate, each amplifier being connected with a respective line of the charge storage devices of the array for converting the stored charge of the respective line of charge storage devices into an analog signal, a stored charge altering means for altering the stored charge on each charge storage device in accordance with an amount of received penetrating radiation, and a plurality of analog to digital converters disposed on the substrate for converting the analog signal to digital values.

13. The radiographic scanner as set forth in claim 12, wherein the array of charge storage devices includes a CCD array and the stored charge altering means includes an array of scintillation crystals for converting received radiation into light, the scintillation crystals being optically coupled to the CCD array such that the light alters the stored charge.

14. The radiographic scanner as set forth in claim 12, wherein the stored charge altering means includes an array of solid state devices which emit charge in response to received radiation, the solid state device array being connected to the array of charge storage devices such that the emitted charge is stored by the array of charge storage devices.

15. The radiographic scanner as set forth in claim 14 wherein the solid state devices include one of photodiodes and photocapacitors which are primarily responsive to optical wavelength radiation and further including an array of scintillation crystals for converting the penetrating radiation into optical wavelength radiation.

16. A detector array comprising:

a plurality of photodetectors connected to a substrate and arranged in an n×m array, where n and m are integers, each photodetector converting light into electrical charge;

a plurality of charge storage devices integrally formed on the substrate for accumulating and storing electrical charge, each photodetector being selectively connected to a respective charge storage device for altering the electrical charge stored thereby in accordance with an amount of light converted into electrical charge;

a plurality of amplifiers connected to the substrate for selectively amplifying the stored charges from the charge storage devices to produce analog electrical signals; and an analog to digital converter disposed on the substrate and connected with the amplifiers for converting the analog electrical signals into digital signals.

17. The detector array as set forth in claim 16, further including a second plurality of charge storage devices integrally formed on the substrate for accumulating and storing electrical charge, each photodetector being alternately connected to the first and second charge storage devices, the amplifiers being connected with the other of the charge storage devices such that one stores charge while the charge on the other is converted into the analog signal.

18. The detector array as set forth in claim 16 wherein the plurality of charge storage devices include n×m array of charge storage devices arranged in columns and rows, charge storage devices of each row being selectively interconnected to form first analog shift registers allowing the stored charge to be shifted along the rows to the amplifiers.

19. The detector array as set forth in claim 16 further including:

a plurality of scintillation crystals arranged in an n×m array, said scintillation crystals converting x-ray radiation into visible light, the n×m array of scintillation crystals being optically coupled to the n×m array of photodetectors.

* * * * *